United States Patent [19]

Richards et al.

[11] Patent Number: 4,895,289
[45] Date of Patent: Jan. 23, 1990

[54] OPHTHALMIC STAPLER

[75] Inventors: William D. Richards, Medway; Ernesto E. Blanco, Belmont, both of Mass.

[73] Assignee: Ophthalmic Ventures Limited Partnership, Norwood, Mass.

[21] Appl. No.: 296,894

[22] Filed: Jan. 12, 1989

Related U.S. Application Data

[63] Continuation of Ser. No. 944,951, Dec. 22, 1986, abandoned.

[51] Int. Cl.⁴ ............................................. A61B 17/00
[52] U.S. Cl. ...................... 227/19; 227/141; 606/138
[58] Field of Search .................... 227/19, 141, DIG. 1

[56] References Cited

U.S. PATENT DOCUMENTS

| | | | |
|---|---|---|---|
| 2,520,973 | 9/1950 | Sorenson | 227/19 X |
| 4,014,492 | 3/1977 | Rothfuss | 227/19 |
| 4,196,836 | 4/1980 | Becht | 227/110 |
| 4,321,002 | 3/1982 | Froehlich | 227/19 X |
| 4,399,810 | 8/1983 | Samules et al. | 227/19 X |
| 4,399,938 | 8/1983 | Biddle | 227/132 |
| 4,523,695 | 6/1985 | Braun et al. | 227/8 |
| 4,526,174 | 7/1985 | Froehlich | 227/19 X |
| 4,527,725 | 7/1985 | Foslien | 227/19 |
| 4,558,810 | 12/1985 | Mulhauser et al. | 227/19 |
| 4,619,262 | 10/1986 | Taylor | 227/19 X |

Primary Examiner—Paul A. Bell
Attorney, Agent, or Firm—Schiller, Pandiscio & Kusmer

[57] ABSTRACT

A stapler system for surgical suturing comprising a novel stapler and novel precurved staples designed for use with the stapler. Staples stored on a magazine are implanted by a ram mounted for reciprocal movement on the body of the stapler. The ram is moved to firing position by a handle pivotally mounted to the stapler body. As the handle is pivoted, a flat spring coupled to the ram is biased. When the ram reaches its firing position, the handle slips from engagement with the ram, thus permitting the biased spring to drive the ram downward so as to implant a staple into the incised tissue. The legs of the staple enter the tissue along a curved path. During implantation the staple is bent around an anvil causing the legs of the staple to penetrate the tissue along a curved path. Insertion of the staple legs along this curved path draws adjacent portions of incised tissue together. Just before the ram reaches the end of its drive stroke, the anvil is automatically withdrawn from between the sutured tissue and the fully implanted staple so as to minimize tissue trauma.

23 Claims, 6 Drawing Sheets

OPHTHALMIC STAPLER

This application is a continuation of Ser. No. 06/944,951 filed Dec. 22, 1986, now abandoned.

FIELD OF THE INVENTION

This invention relates to methods and devices for suturing delicate tissue, and more particularly to an improved method and means for inserting fine wire staples into incised tissue.

BACKGROUND OF THE INVENTION

In most surgical operations, suturing an incision in tissue typically consumes a large portion of the total operating time. Stapling devices for surgical suturing have been developed to reduce this suturing time. Examples of surgical stapling devices are provided by U.S. Pat. Nos. 3,604,561, 3,646,801, 4,162,678, 4,316,468, 4,317,451, and 4,485,816.

Conventional suturing staplers suffer from several problems. For one thing, many of the staplers are relatively large, which tends to limit their usefulness for delicate surgical procedures. Also, known suturing staplers typically bend the legs of the staple around a fixed rectangular staple anvil during insertion of the staple into the tissue. This simultaneous bending and insertion often causes the tissue adjacent the incision to tear, thereby inducing potentially severe traumatic effects. In addition, the fixed anvil is typically positioned to rest on the tissue surface. Hence, after stapler actuation is completed and the staple is fully implanted, the fixed anvil typically remains sandwiched in tight compression between the staple and the tissue surface, so that removal of the anvil tends to abrade or otherwise injure the tissue surface, thereby inducing further trauma. These anvil-related characteristics make such known staplers undesirable for delicate surgery.

OBJECTS OF THE INVENTION

A primary object of the present invention is to provide a suturing stapler system of a size suitable for use in delicate surgeries wherein precurved staples are inserted into incised tissue along a curved path in a manner causing the adjacent edges of incised tissue to be drawn together with minimal compacting and tearing of the tissue.

Another primary object of this invention is to provide a suturing stapler system for implanting staples in incised tissue having a mode of operation whereby the two legs of each staple are bent over a curved anvil during insertion into the tissue on opposite sides of the incision, the two legs of the staple being drawn together during this bending along a curved path so as to cause the tissue to be brought together to close off the incision.

Still another primary object of this invention is to provide a surgical suturing stapler having means for automatically removing the anvil from its position between the incised tissue and the staple in the final stages of staple insertion in a manner that minimizes abrasion and pulling of the tissue.

An additional object of this invention is to provide a stapler for surgical suturing that is made of relatively inexpensive materials and has a simple construction, thereby permitting it to be manufactured at a relatively low cost.

A further related object is to provide a stapler that is easily assembled so as to facilitate staple loading.

Still another object is to provide a novel form of staple that is shaped so as to render it especially useful for surgical suturing applications.

Another object is to provide an improved method of implanting staples.

SUMMARY OF THE INVENTION

These and other objects of this invention are achieved by a stapler system comprising (1) novel staples having a selected curved configuration and (2) a stapler designed for implanting the novel staples in a novel manner. The stapler is constructed for implanting the staples in incised tissue along a curved path. The staples retain their original preformed shape during a first portion of the implantation process as the staples are transported from their staple magazine to a position immediately adjacent the incised tissue. Later in the implantation process the stapler deforms the curved spine or bridge section of the staple so as to cause the two legs of the staple to be drawn together along a curved path, thereby causing the legs of the staple to penetrate the incised tissue and bring the two edges of the incision tightly together in a manner almost identical to what occurs when using a conventional curved-needle and thread suturing procedure. In the final stage of the staple implantation process, the anvil portion of the stapler is driven from its position between the tissue surface and the fully inserted staple.

The stapler for performing this procedure includes a body and a staple driving ram reciprocally mounted on the body. A handle, pivotally mounted on the frame, is releasably coupled to the ram for moving the ram away from the tissue surface. This movement of the ram biases a spring coupled to the ram. Staple storage and feed means are provided for feeding a staple into the path of the driving edge of the ram. Actuation of the handle moves the ram even farther away from the tissue surface until a point is reached where the handle separates from the ram, whereupon the biased spring rapidly drives the ram down against the leading staple so as to propel that staple at high velocity into the tissue. As the staple approaches a fully implanted condition, it encounters an anvil that coacts with the descending ram so as to cause the two legs of the staple to be drawn together. In the final stage of staple insertion, the anvil is automatically driven out of contact with the staple as the staple's implantation is completed by the ram.

Other objects of the invention are hereinafter described or rendered obvious. In any event the invention comprises apparatus possessing a construction, combination of elements, and arrangement of parts as exemplified in the following detailed disclosure or as encompassed by the claims.

BRIEF DESCRIPTION OF THE DRAWINGS

For a fuller understanding of the nature and advantages of the present invention, reference should be had to the following detailed description taken in connection with the accompanying drawing(s) wherein.

In the drawings, like parts are identified by like numerals.

DETAILED DESCRIPTION OF THE PREFERRED EMBODIMENT

Figure 1:
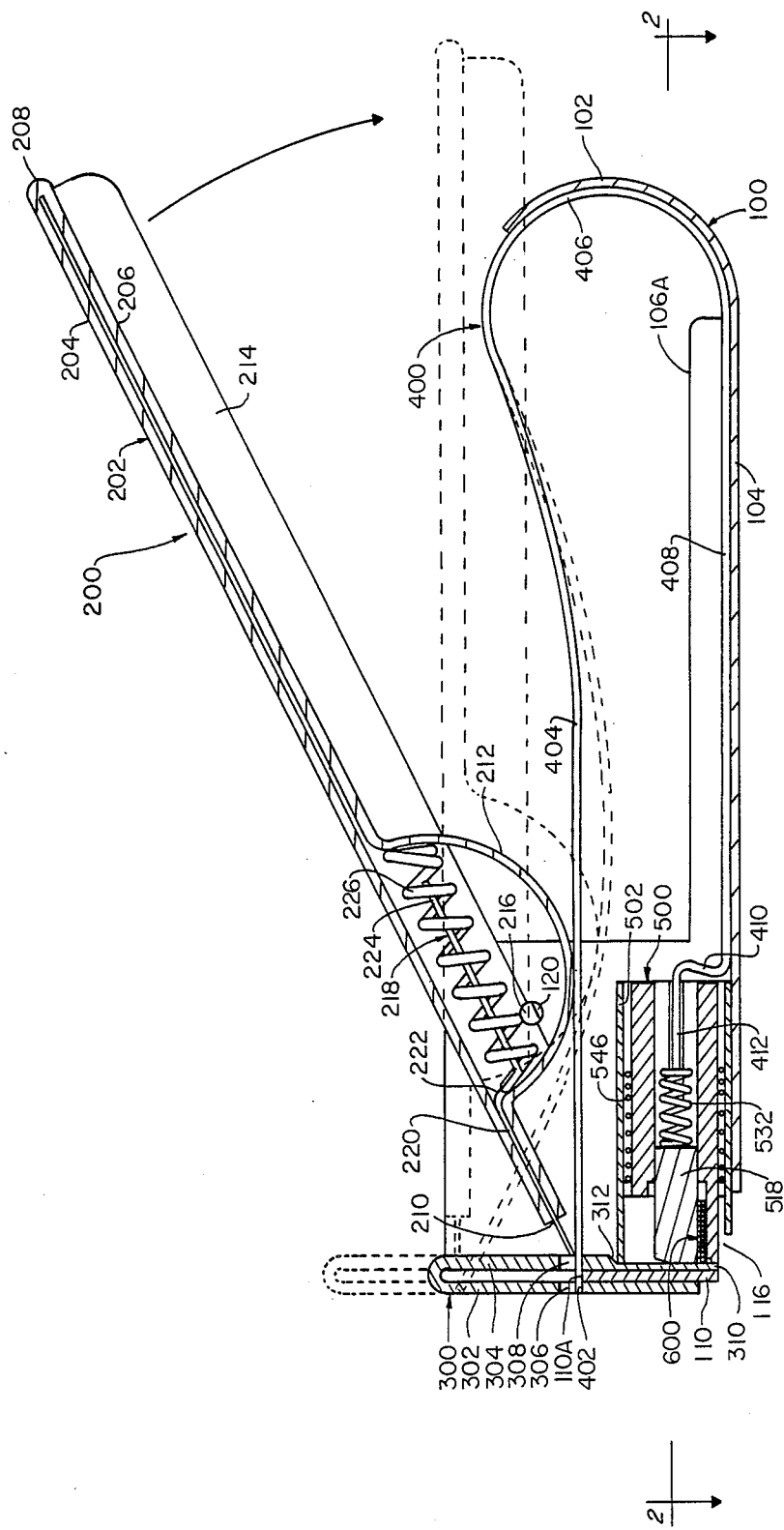
FIG. 1 is a longitudinal sectional view of a stapler constituting a preferred form of the invention in its at-rest position, with various parts of the invention being shown in full view for the sake of clarity.

Referring to FIG. 1 for a brief description of the invention, a stapler system for surgical suturing is shown. The stapler includes a body 100, an actuating means 200, a ram 300, a flat ram-driving spring 400, and a staple magazine 500 that stores a plurality of staples 600 designed for use with the stapler.

Figure 2:
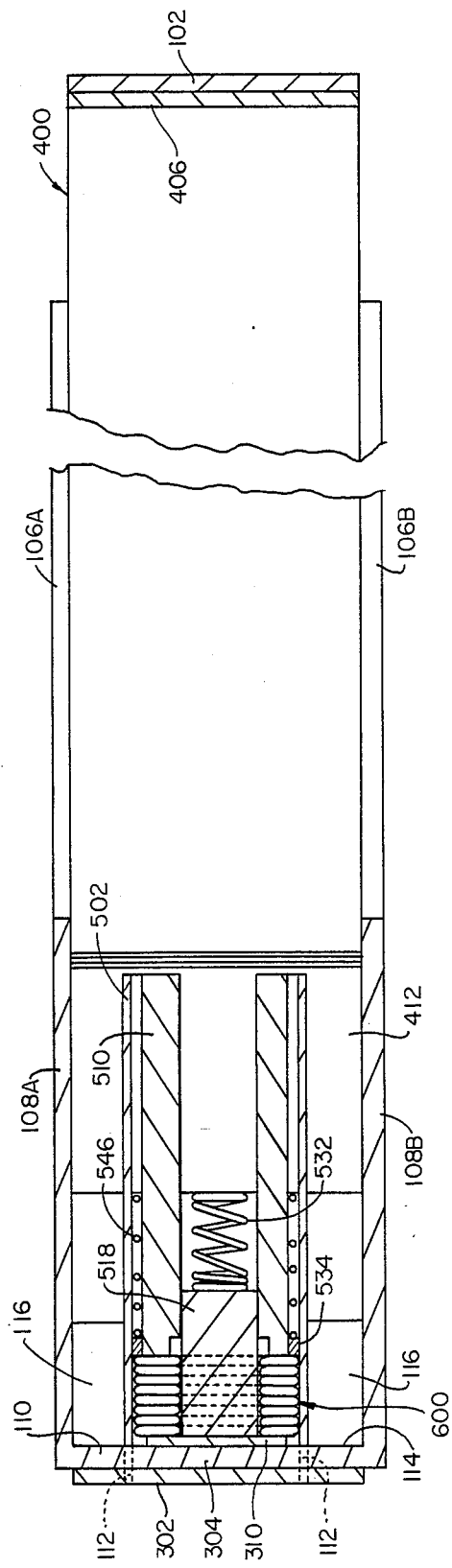
FIG. 2 is an enlarged section view taken along lines 2—2 of FIG. 1.

Turning now to FIGS. 1-4, the stapler body 100 preferably is formed out of one piece of sheet metal that is cut and bent so as to comprise a curved rear wall 102, a bottom wall 104, a pair of rear side walls 106A and 106B, a pair of front side walls 108A and 108B that are extensions of rear side walls 106A and 106B, and a front wall 110 having a top surface 110A. The side walls 106A, 106B and 108A, 108B extend substantially at right angles to bottom wall 104 and front wall 110. Front wall 110 has two identical vertically-extending narrow slots 112 formed therein (as shown in phantom in FIG. 2) and a rear surface 114. The forward end of bottom wall 104 terminates short of front wall 110 so as to form a bottom aperture 116 (FIGS. 1 and 2). Additionally, the bottom portions of front side walls 108A and 108B are cut away as shown at 118 (FIG. 3) so as to form side openings for aperture 116. Identical circular holes 120 are formed in front side walls 108A and 108B (only one of the two aligned holes 120 is visible, in FIG. 1).

Referring again to FIG. 1, actuating means 200 comprises a handle 202 preferably formed from one piece of sheet metal that is arranged so as to form a flat top wall 204 that extends substantially parallel to a major portion of a bottom wall 206 and a curved rear wall 208 that joins walls 204 and 206. The forward end of the handle is characterized by a flat opening 210 between walls 204 and 206. A portion of bottom wall 206 is formed with a circularly curved bulge 212 that serves as a cam. The handle also has a pair of opposite side walls 214 (only one of which is visible in FIG. 1). Side walls 214 extend substantially perpendicular to walls 204 and 206. Each side wall 214 is deformed at its bottom edge so as to form an outwardly facing bulge or trunnion detent 216 that is sized so as to make a close fit in one of the holes 120. Bulges or trunnions 216 act as pivot tabs that coact with holes 120 to pivotally secure the handle 202 to body 100.

Actuating means 200 also comprises finger member 218 formed of a flat piece of sheet metal. Finger member 218 is bent so as to have a straight front section 220 that is offset from a straight rear section 224 by a non-parallel connecting section 222. Front finger section 220 extends between and makes a close sliding fit with the front end portion of handle walls 204 and 206, thereby permitting finger member 218 to slide back and forth lengthwise of handle 202. The forward end of finger section 220 protrudes out of flat opening 210 a selected distance when handle 202 is in the at-rest position shown in FIG. 1.

Finger 218 is biased toward opening 210 by a compression spring 226 that is mounted in the space formed between top wall 204 and cam bulge 212. Spring 226 is captivated between opposite side walls 214 of the handle. The rear end of spring 226 contacts the inner surface of cam bulge 212, while its forward end contacts the bent connecting section 222 of finger member 218. Compression spring 226 urges finger member 218 into engagement with the forward end of cam bulge 212, while permitting it to slide in the opposite direction when subjected to a force sufficient to overcome the bias of the spring. When the stapler is in its at-rest position (FIG. 1), the bent section 222 of the finger is held against the forward end of cam bulge 212, and the front section 220 of the finger protrudes from opening 210 as shown.

Figure 6:
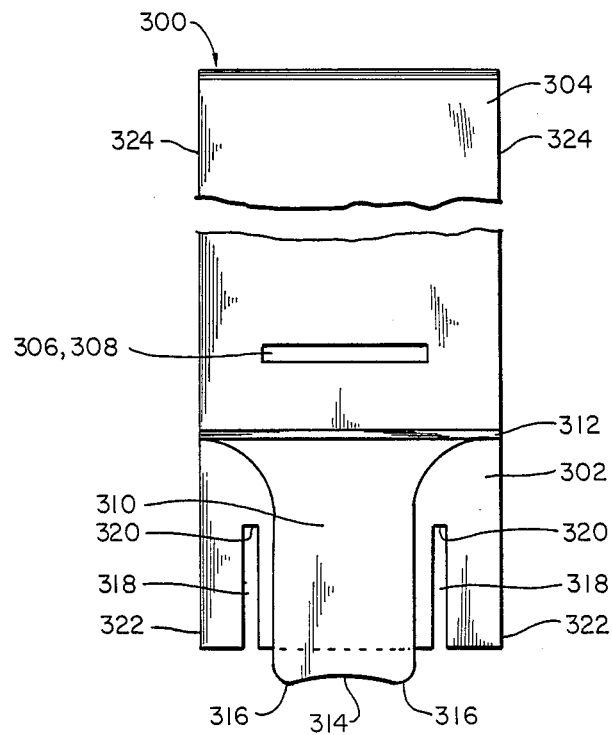
FIG. 6 is a rear elevation of the ram.

Turning next to FIGS. 1-3 and 6, the ram 300 is preferably formed of one piece of sheet metal that is folded into a U-shape so as to provide a front portion 302 and a rear portion 304. Front portion 302 extends parallel to and is spaced apart from rear portion 304. As seen in FIGS. 1 and 6, mutually aligned slots 306 and 308, of substantially identical size and shape, are formed in portions 302 and 304, respectively. The bottom end of rear portion 304 is flattened and reduced in thickness (see FIGS. 1 and 3) so as to form a driving section 310. A shoulder 312 is formed at the junction of driving section 310 and the upper section of rear portion 304. A circularly curved striker edge 314 (FIG. 6) is formed on the bottom end of driving section 310, the edge 314 terminating in like shoulders 316. Two parallel vertically-extending slots 318 (see FIG. 6) are formed in ram front portion 302 commencing at its bottom edge. Slots 318 extend at a right angle to slots 306 and 308 and terminate at top surfaces 320. The side edges 324 of the upper section of rear portion 304 extend substantially parallel to the side edges 322 of front portion 302.

Looking next at FIG. 1, the flat ram-driving leaf spring 400 is formed so as to have a forward ram biasing top end portion 402, an elongate cam-contacting portion 404, a curved rear end portion 406, a main bottom portion 408, a bent forward bottom portion 410, and a spring contact bottom front end portion 412. Ram biasing end 402 is reduced in width relative to the remainder of spring 400 so as to make a relatively loose fit in slots 306 and 308 of ram 300.

Figure 3:
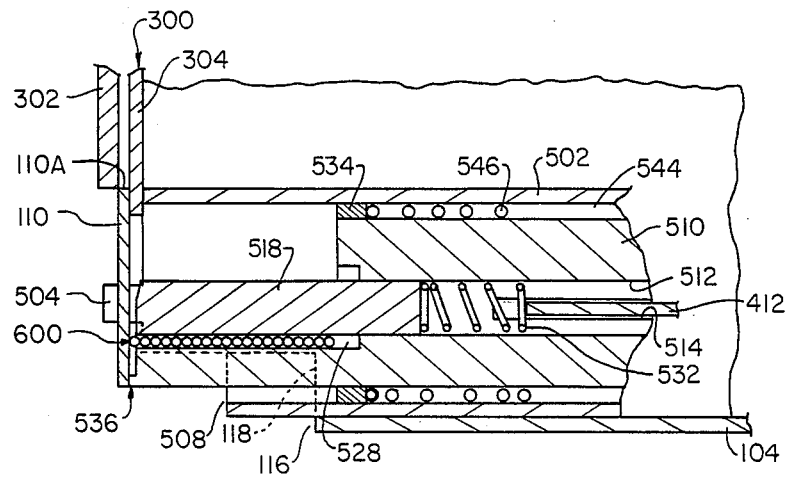
FIG. 3 is an enlarged view of a portion of FIG. 1.
Figure 4:
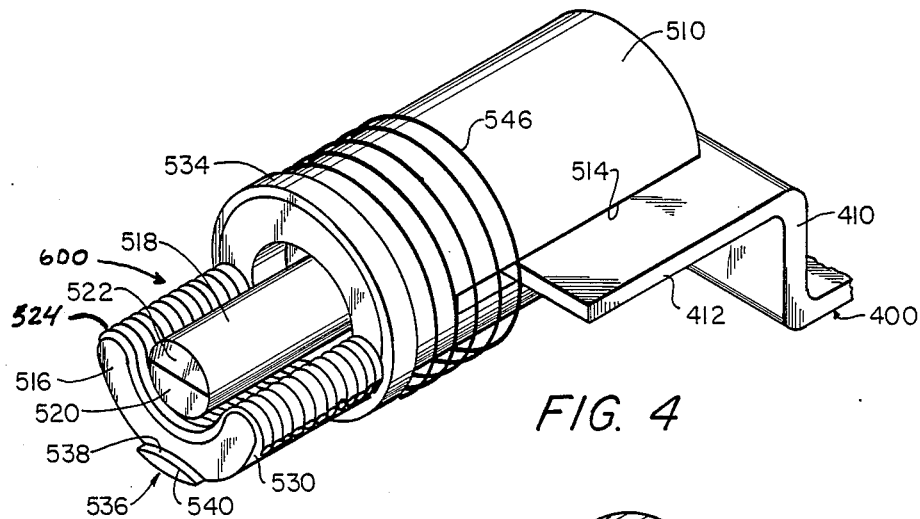
FIGS. 4 and 5 are perspective views showing portions of the same stapler.
Figure 5:
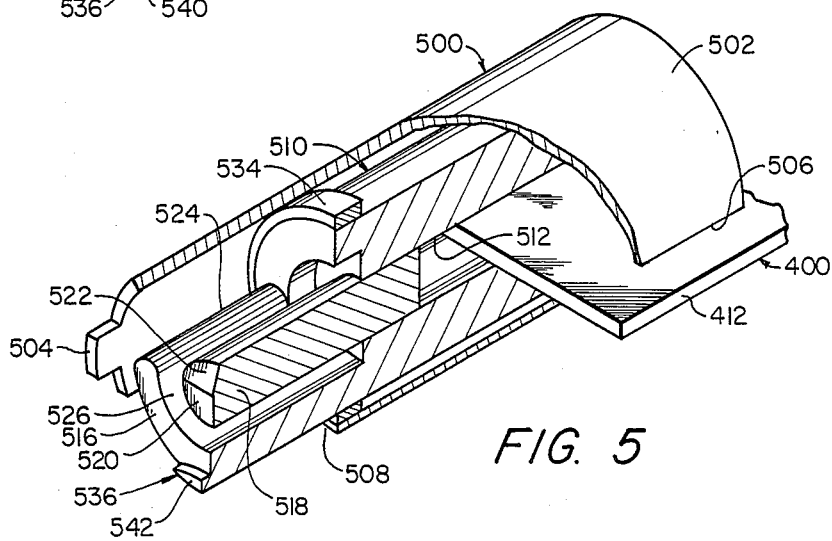

Turning now to FIGS. 1-5 and 7, the magazine 500 comprises a hollow cylinder 502 shaped for containing the various other elements of the magazine described below. Cylinder 502 has two fingers or dowels 504 (only one of which is shown, in FIGS. 3 and 5) integral with and extending forwardly from its front end. As seen in FIG. 5, a horizontal diametrical slot 506 is formed in cylinder 502. Also, the forward end of the cylinder is cut back on its bottom side so as to provide a slot 508 (FIG. 5).

A cylindrical mandrel 510 (FIGS. 3-5) is slidably mounted inside hollow cylinder 502. Mandrel 510 has an axial bore 512 intersected at its rear end by a horizontal diametrical slot 514 (FIGS. 3-5). Mandrel 510 has a flat face 516 that extends vertically and in parallel with front wall 110 of body 100. A rod 518 is press-fit in the front end of bore 512 so as to form an integral assembly with mandrel 510. Rod 518 has a flat vertically-extending front face 520 (FIGS. 4 and 5), with the upper portion 522 (FIGS. 4 and 5) of face 520 being inclined with respect to the remainder of that face and also with respect to front wall 110 of body 100. The length of rod 518 is such that flat face 516 of mandrel 510 and front face 520 of rod 518 lie along the same vertically-extending plane.

Figure 7:
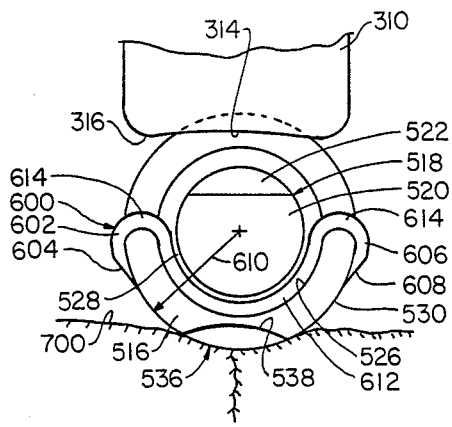
FIGS. 7, 9, 11, 13, and 15 are schematic end views in elevation of the mandrel, ram, and staple showing the various stages of staple implantation using the staples and stapler of the present invention.

Mandrel 510 serves to store a supply of staples and for that purpose it has a forward staple-mounting portion 524 (FIG. 5). The latter has a U-shaped cross-section corresponding to the profile of the staples intended to be used with the stapler. Portion 524 has a top groove characterized by a generally circularly curved concave top surface 526 (FIG. 5) and a convexly curved outer surface 530 (FIGS. 4 and 7). Rod 518 is disposed within the top groove of forward portion 524 and is radially spaced from top surface 526 so as to form a cavity 528 (FIG. 3) having a half-cylinder shape.

A compression spring 532 (FIGS. 1–3) is mounted in bore 512. The forward end of spring 532 contacts the rear end of rod 518, while its opposite end engages the forward end of section 412 of leaf spring 400. A flat ring 534 (FIGS. 3–5) is slidably disposed in cylinder 502 so as to slidably surround mandrel 510.

Integrally formed on the front end of mandrel 510 is an anvil 536. The latter protrudes a selected distance from flat face 516 and has a circularly curved upper surface 538 that preferably extends substantially perpendicular to flat face 516, a front edge 540 (FIG. 4), and a front face 542 (FIG. 5) that extends substantially parallel to flat face 516.

When mandrel 510 is positioned in cylinder 502, the difference between the outside diameter of the mandrel and the inside diameter of the cylinder forms a cylindrical cavity 544 (FIG. 3). A coiled compression spring 546 is positioned in cavity 544 in surrounding relation with mandrel 510. The front end of spring 546 contacts flat ring 534, while its rear end is engaged by the front end 412 of spring 400 (see FIG. 4).

Referring now to FIG. 7, the staples 600 designed for use with the present stapler are made of fine wire of circular cross-section. Each staple comprises a pair of circularly curved legs 602 and 606 each having at their inner sides a radius of curvature only slightly greater than the radius of curvature (indicated at 610) of the surface 530 of the staple mounting portion 524 of cylindrical mandrel 510. Legs 602 and 606 have pointed ends 604 and 608, respectively, and the curved legs extend so that the ends 604 and 608 point straight down or, more preferably, begin to converge toward one another. Legs 602 and 606 are connected together by concavely curved bridge section 612. Bridge section 612 has a curvature that closely conforms to the shape of the upper surface 526 of forward portion 524 of mandrel 510. Bridge section 612 is shaped so as to coact with anvil 536 and ram 300 during insertion of the staple, in a manner described below. The staples also have curved shoulders 614 at the junctions of legs 602 and 606 with bridge section 612. The shape of legs 602 and 606 and shoulders 614 closely conforms to the shape of outer surface 530 of front portion 524. On account of the foregoing construction, it will be appreciated that the staples 600 are supported along substantially their entire length by upper surface 526 and outer surface 530. Several of the leading staples 600 supported on mandrel 510 have been removed in FIG. 4 to illustrate the relationship between the configuration of the staples and the configuration of the surface of the mandrel on which they are supported. Of course, ordinarily the staples 600 will be supported along the entire length of mandrel 510, as illustrated in FIG. 3. As noted above, upper surface 526 is radially spaced from rod 518 so as to form cavity 528. The radial spacing between upper surface 526 and the outer surface of rod 518 is slightly greater than the cross-sectional diameter of staples 600, whereby rod 518 and upper surface 526 together serve as a guide assembly for ensuring staples 600 are properly aligned on mandrel 510. The diameter of the wire used to make the staples 600 is preferably approximately one-third to one-half the diameter of a conventional curved suturing needle, i.e., preferably between about 0.002 and 0.003 inches for staples used for ophthalmic or plastic surgery. While other materials may be advantageously used, stainless steel wire is the preferred material because of its strength, malleability, and anti-corrosion properties.

Turning again to FIG. 1, the various elements of the stapler system described above are positioned relative to one another, and cooperate with one another, in the following manner. Spring 400 is mounted in body 100 so that its bottom portion 408 lies flat against body bottom portion 104 and its curved portion 406 lies flat against the curved body rear portion 102. The width of spring 400 is only slightly less than the distance between side walls 106A and 106B and 108A and 108B, so that the former two walls limit lateral movement of the spring relative to the body 100, while still permitting slidable movement of the portion 404 of spring 400 relative to side wall portions 108A and 108B.

Ram 300 is mounted for slidable movement on front wall 110, with its front and rear sections 302 and 304 straddling wall 110. The gap distance between sections 302 and 304 is set so that they slidingly engage wall 110. Ram portion 310 extends down between dowels 504 of cylinder 502, with front side walls 108A and 108B restraining the ram against sideways movement. Ram 300 normally occupies its bottom limit position between anvil 536 and wall 110 (FIG. 1) but is capable of being moved to a predetermined raised release position (shown in phantom in FIG. 1) by operation of handle 202 as hereinafter described.

The front end 402 of leaf spring 400 extends over wall 110 into slots 306 and 308 of ram 300. As noted above, the width of front end 402 is selected to make a relatively loose fit in slots 306 and 308. Spring 400 exerts a downward bias on the ram, forcing it to assume its bottom limit position (FIGS. 1 and 16), in which position the bottom edges of slots 306 and 308 are aligned with the top edge 110A of front wall 110, and the bottom surface of the front end 402 of spring 400 contacts the top edge 110A of wall 110. The front end 402 of spring 400 remains engaged in slots 306 and 308 of ram 300 as the latter is raised and released by operation of handle 202.

The handle 202 of actuating means 200 is pivotally mounted to body 100 as a result of insertion of pivot trunnions 216 in holes 120. The width of handle 202 measured between the outside surfaces of its side walls 214 is selected so that those outside surfaces will make a close sliding fit between body side walls 108A and 108B and so that they must be compressed toward one another in order to permit pivot trunnions 216 to snap into holes 120. The pivot trunnions are sized so that they can rotate in holes 120. As a consequence, handle 202 is pivotally supported by side walls 108A and 108B and is insertable therebetween by spreading resilient side walls 108A and 108B apart so as to permit the handle to be mounted in the stapler.

When the handle is pivotally mounted to body 100 in the manner shown in FIG. 1, the forward end of section 220 of finger member 218 extends into slot 308 above the forward end of spring 400. As handle 202 is pivoted toward body 100 in the direction shown by the arrow in FIG. 1, finger member 218 acts on the upper edge of slot 308 to force the ram upwardly relative to wall 110. As it forces the ram to move upwardly, the forward end of finger member 218 moves through a circular arc. As the forward end section 220 of finger member 218 passes above the horizontal, it begins to move out of slot 308. Eventually, as the handle pivots still further, finger member 218 slips out of slot 308, thereby freeing the ram for downward return movement under the influence of spring 400.

As seen in FIG. 1, the cam bulge 212 of handle 202 is always in contact with the upper portion 404 of spring 400. As the handle 202 is moved so as to raise ram 300, cam bulge 212 forces spring portion 404 to bow downwardly at the same time that the forward end 402 of the spring is forced to follow the upward movement of ram 300 caused by finger member 218. This deformation of spring 400 causes it to exert a downward bias on ram 300. Consequently, when ram 300 has moved upward far enough for the forward end of finger member 218 to slip out of slot 308, the energy stored in spring 400 by its deformation will act to drive ram 300 downward at a relatively high velocity back to its bottom limit position, whereby a staple will be discharged and implanted in a manner hereinafter described. Upon subsequent release of handle 202, spring 400 will cause the handle to pivot counterclockwise (as seen in FIG. 1) back to its original at-rest position.

As ram 300 is rapidly driven downward, the forward end of finger 218 remains in sliding contact with the rear surface of rear ram portion 304, and when handle 202 is released and allowed to pivot counterclockwise back to its original at-rest position, spring 226 will allow finger member 218 to retract into the handle far enough to allow the handle to pivot unimpeded under the influence of spring 400. In the course of this return movement of the handle, the forward section of finger 218 will again reach the level of slot 308, whereupon spring 226 will urge it back into slot 308. The exact point at which this reengagement occurs depends, of course, upon the positioning and configuration of slot 308 and the front end of finger 218.

Referring now to FIGS. 1-6, magazine 500 is positioned in body 100 adjacent aperture 116 with the forward end 412 of spring 400 extending into cylinder slot 506 and mandrel slot 514 and acting on spring 532 to urge mandrel 510 and rod 518 toward front wall 110. The forward end 412 of spring 400 also urges hollow cylinder 502 forward so as to keep its fingers 504 (FIGS. 3 and 5) fixed in ram slots 318 (FIG. 6) and body apertures 112 (FIG. 2). Fingers 504 thus act to retain magazine 500 in right angle relation with front wall 110 so as to assure proper axial travel of the staples on mandrel portion 524.

It is important to the operation of the invention that the downward travel of ram 300 be stopped at a proper limit position. To this end, slots 318 are sized so that fingers 504 engage the top surfaces 320 of the slots just as the ram reaches its bottom limit position (as seen in FIG. 1).

As noted previously, spring 532 urges mandrel 510 and rod 518 toward front wall 110. Under this urging, anvil 536 contacts the rear surface of front wall 110 during a substantial portion of the reciprocating stroke of ram 300 produced by squeezing handle 202.

Figure 8:
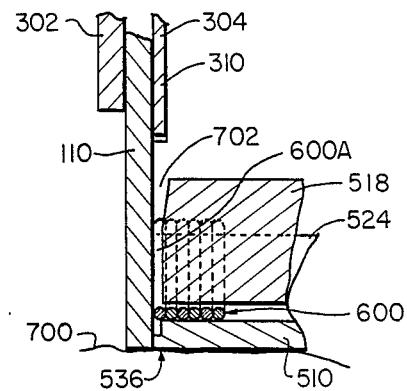
FIGS. 8, 10, 12, 14 and 16 are schematic side views in elevation corresponding to FIGS. 7, 9, 11, 13 and 15, respectively.

As noted above, compression spring 546 is disposed in cavity 544 so that the forward end of the spring engages flat ring 534 and its rear end engages the forward end section 412 of spring 400 (FIG. 4). Flat ring 534 engages the last staple of the plurality of staples 600 mounted on mandrel portion 524. Under the bias of spring 546, flat ring 534 slides within cylinder 502 and over mandrel 510 and thereby urges the plurality of staples 600 toward front wall 110 and ram 300. When the ram is at rest in its lower limit position (FIGS. 1 and 16), its staple driving section 310 extends between front wall 110 and anvil 536, and the first one of the staples 600 is held against the rear surface of ram driving section 310 by spring 546. As ram 300 is raised by squeezing handle 202, a point is reached (FIGS. 7 and 8) whereupon the driving section 310 of ram 300 resides above the front staple 600A of the plurality of staples 600, with the result that spring 546 pushes the front staple off of curved mandrel section 524 up against the rear surface of wall 110, in center line alignment with anvil 536.

Figure 12:
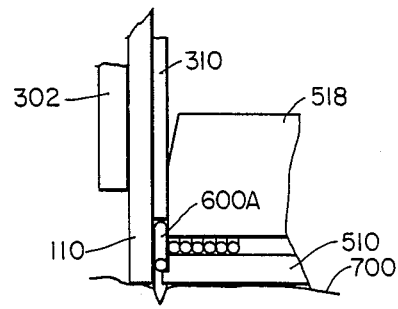
Figure 13:
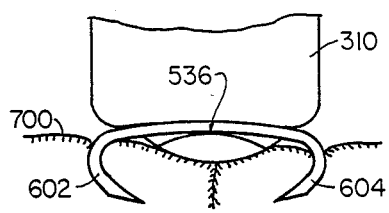
Figure 14:
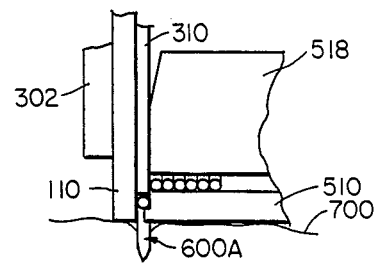

Upon disengagement of ram-moving finger 218 from ram slot 308, spring 400 drives the bottom edge 314 of ram staple driving section 310 (FIG. 6) into contact with the front staple 600A engaged with front wall 110, causing that staple to move downwardly into the vertically extending cavity 702 (see FIG. 8) formed between front wall 110 and inclined upper rod face 522. When ram 300 is raised high enough for anvil 536 to contact front wall 110 (FIGS. 3 and 8), the distance between the rear surface of front wall 11 and front face 516 of mandrel 510 is less than the thickness of staple 600A. However, because surface 522 is inclined, the distance between the rear surface of front wall 110 and the upper edge of surface 522 is slightly greater than the thickness of a staple 600. As such, the front staple 600A can be driven downward into cavity 702 by ram 300. As this occurs, the ram coacts with inclined surface portion 522 to force mandrel 510 and rod 518 axially away from ram 300. This rearward axial movement of mandrel 510 enlarges cavity 702 enough to permit staple 600A to slide down between front wall 110 and mandrel flat face 516 as it is driven toward anvil 536 (in FIGS. 10, 12 and 14, cavity 702 has been enlarged by coaction of staple 600A with front wall 110 and mandrel flat face 516). Under the bias of spring 532, mandrel face 516 urges staple 600A against the rear surface of front wall 110 with sufficient force to control the movement of staple 600A toward anvil 536 so that pointed ends 604 and 608 of staple 600A (FIG. 7) enter the subject tissue at substantially the same instant.

Figure 9:
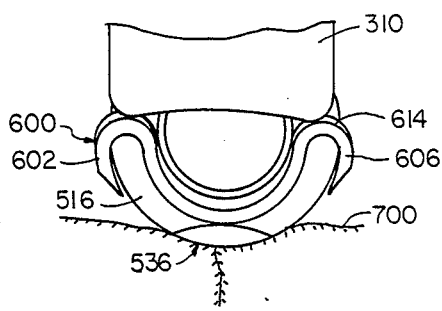
Figure 10:
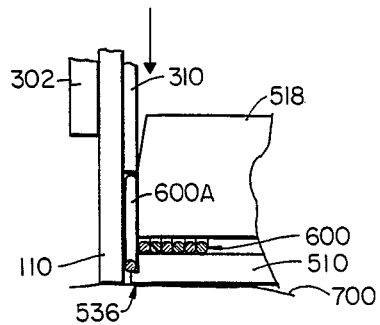
Figure 11:
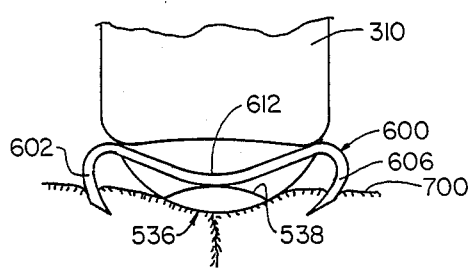

Referring now to FIGS. 3-5 and 7-16, the first staple in dispensing position is initially driven downwardly by engagement of ram shoulders 316 with staple shoulders 614. The staple is driven downwardly so that the center of its bridge section 612 engages the center of the curved upper anvil surface 538, as shown in FIGS. 9 and 10. No deformation of the staple occurs during this initial movement as the staple moves down to meet the anvil. Continued downward movement of the ram 300 beyond the point at which this contact first occurs causes the staple bridge section 612 to flatten and the legs 602 and 606 to move toward one another along curved paths having radii of curvature in close approximation to the radii of curvature of the legs in their initial preformed condition, as shown in FIGS. 9 and 11. As shown in FIGS. 11-14, further downward movement of ram 300 causes legs 602 and 606 to enter tissue 700 and causes bridge section 612 to bend around the curved anvil surface 538. Finally, a point is reached where further downward movement of the ram 300 causes bridge 612 to coact with the anvil front edge 540 (see FIG. 4) and the rear surface of front wall 110. This coaction drives mandrel 510 even further away from ram 300 (see FIGS. 14 and 16) to a point where anvil 536 is driven from beneath the staple bridge 612 and the driving end 310 of the ram is sandwiched between front wall 110 and anvil front surface 542 (see FIG. 16). This position is the bottom limit position of the ram, i.e., the end of its staple driving stroke. As noted previously, downward movement of ram 300 is stopped by engagement of fingers 504 with top surfaces 320 of slots 318.

Assembly first involves sliding mandrel 510 out of cylinder 502 far enough to expose the grooved front section 524. Staples 600 are then placed on front section 524 so as to be positioned in cavity 528 (FIG. 3). The loaded magazine 500 is then slid onto spring end 412 of leaf spring 400. Magazine 500 and leaf spring 400 are then inserted as a unit into body 100 so that curved rear end portion 406 of the spring engages curved rear portion 102 of body 100. Next, ram 300 is inserted by positioning spring end 402 into ram slots 306 and 308 and by placing ram portions 302 and 304 on opposite sides of front wall 110. Finally, handle 202 is attached by inserting front finger section 220 into slot 308 in ram 300 and inserting pivot trunnions 216 into holes 120 by forcing body side wall portions 108A and 108B apart.

The stapler offers the advantage that it can be made quite small, so that handle 202 and bottom wall 104 may be grasped by the thumb and fingers of the surgeon, e.g. the stapler's overall length may be approximately 0.75-1.25 inch.

To increase control of the stapler during the suturing procedure, body 100 may be attached to a conventional surgical needle holder or to an extension handle adapted to grip body 100. No extension or auxiliary handle need be attached to handle 202 when body 100 is attached to a needle holder or to an extension handle.

In operation, the stapler is loaded with staples 600 and then reassembled in the manner previously described. Then the stapler is positioned so that (a) front wall 110 and anvil 536 rest on the tissue 700 to be sutured and (b) staple legs 602 and 606 of the first staple 600A are disposed on opposite sides of the incision to be sutured. Aperture 116 (FIG. 11), cutaway portions 118 (FIG. 3), and slot 508 (FIG. 5) assure that the stapler has no sharp corners where it is placed in contact with the tissue surface. The aperture 116 and slot 508 are also necessary to provide openings in body 100 and cylinder 502, respectively, for ejecting staples 600. Once the stapler is properly positioned relative to the incision, a staple is implanted by squeezing handle 202 so as to pivot its end 208 clockwise, as seen in FIG. 1. This raises ram 300 upwardly from between wall 110 and mandrel 510 to the position shown in phantom in FIG. 1 and allows the first staple 600A to move forward into the cavity 702 (FIG. 8) against front wall 110 (FIG. 3).

Thereafter, when the front end of finger 218 slips out of slot 308, spring 400 drives ram 300 rapidly down toward the aligned staple 600A. Ram shoulders 316 contact staple shoulders 614 and drive the staple 600A into sliding engagement with mandrel flat face 516 (see FIGS. 4, 9 and 10). Under the driving force of spring 400, ram driving section 310 acts on inclined rod face 522 to drive mandrel 510 and rod 518 axially back away from front wall 110, thereby permitting the staple to slide down along mandrel flat face 516.

Further downward movement of ram 300 drives bridge section 612 against the convex anvil surface 538 and thereby causes the bridge section to bend around the anvil 536 (see FIGS. 9-12). By this bending, the legs 602 and 606 are driven into the tissue along curved paths having radii of curvature close to the radii of curvature of the legs. As the staples enter the tissue along these curved paths, they draw the adjacent edges of the incision together. This curved path is substantially identical to the path followed by a curved needle in the conventional thread suture procedure.

Implanting the staples 600 in this fashion also draws the edges of the incised tissue closer together in a manner almost identical to the way in which tissue is drawn together using the conventional curved-needle suture procedure. Because the round wire staples 600 may have a cross-sectional diameter approximately one-third to one-half the diameter of conventional curved suturing needles, suturing trauma associated with staple implantation is reduced to a level well below the level occurring in conventional curved-needle suturing procedures.

Figure 15:
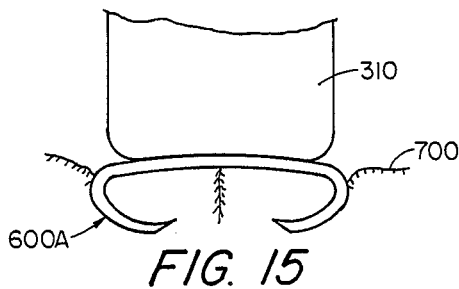
Figure 16:
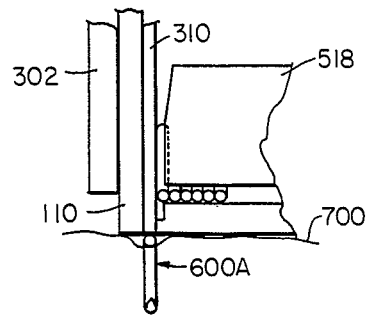

After the staple 600A is almost fully implanted, but before ram 300 reaches its lower limit of travel, anvil 536 is sandwiched between the incised tissue and the bridge 612. In this position (FIGS. 13 and 14), the tissue is slightly depressed beneath the anvil and curved anvil surface 538 contacts only a relatively small portion of the staple bridge section 612. In the final stage of movement of ram 300, staple 600A coacts with front anvil edge 540 to rapidly urge anvil 536 away from front wall 110, thereby retracting the anvil from its sandwiched position between the staple and the tissue (FIGS. 15 and 16). Retraction of anvil 536 permits ram 300 to reach its lower limit position in which the upper edges 320 of slots 318 engage dowels 504. During this final movement, ram 300 finishes its implantation of staple 600A (FIGS. 15 and 16). Removal of anvil 536 also permits the depressed incised tissue to spring back to contact the bottom surface of staple bridge section 612.

Because of the relatively small contact area between staple 600A and anvil 536, and because the anvil is automatically withdrawn in rapid fashion from the sandwiched position between the staple and the tissue, the amount of tissue pulling and tearing associated with anvil removal is greatly reduced as compared to conventional suturing staplers. Moreover, the automatic retraction of the anvil 536 increases the rate at which tissue can be sutured, since upon completion of operation of the stapler, the stapler can be moved to a new suturing site without first pulling the anvil out from its sandwiched position.

Because the stapler is preferably quite small, i.e., having an overall length of about one inch, ram 300 and staples 600 have a relatively small mass and thereby are adapted to be driven at very high velocities. The bias of spring 400 is such that, in view of the relatively small mass of staples 600 and ram 300, staples 600 are driven into tissue 700 with a velocity sufficient to exceed the dynamic resiliency of the tissue. Consequently, little or no deformation or compacting of tissue 700 occurs upon staple insertion, whereby suturing trauma is minimized.

Modifications Of The Preferred Embodiment

While sheet metal (preferably stainless steel sheet metal) is the first choice of material for the manufacture of the stapler, i.e., body 100, handle 202, finger 218, ram 300, and flat spring 400, other materials known to skilled practitioners could also be advantageously used. Sheet metal is preferred because of its relatively low cost and because it can be easily fabricated to form the various elements of the invention. Stainless steel also is the preferred material for the staples.

It is also contemplated that anvil 536 could be formed so that its circularly curved upper surface 538 is inclined slightly front to back, rather than extending substantially perpendicular to flat face 516, as described above.

Since certain changes may be made in the present suturing system described above without departing from the scope of the present invention, it is intended that all matter contained in the preceding description or shown in the accompanying drawings shall be interpretted in an illustrative and not in a limiting sense.

What is claimed is:

1. A stapler system for suturing tissue, said system comprising a stapler and a plurality of staples adapted to be implanted by said stapler,
    each of said staples having two legs connected together by a concave bridge, said legs being curved and having pointed ends; and
    said stapler comprising:
    a body having a staple ejection aperture;
    staple supporting means for slidably supporting said plurality of staples so that the latter can be slidably moved along a path terminating at a predetermined staple ejection position, said staple supporting means being adapted for reciprocal movement within said body into and out of a first position;
    staple advancing means for urging said plurality of staples carried by said staple supporting means toward said predetermined staple ejection position when said staple supporting means is in its said first position so that leading ones of said plurality of staples are successively delivered to said predetermined staple ejection position;
    an anvil carried by said staple supporting means, said anvil being disposed in line with a leading one of said plurality of staples located in said staple ejection position when said staple supporting means is in its said first position;
    biasing means for yieldably positioning said staple supporting means in its said first position; and
    selectively actuatable staple ejecting means movably mounted to said body for driving a staple located in said staple ejection position out of said staple ejection position through said staple ejection aperture, said staple ejecting means comprising a staple driving ram that undergoes a drive stroke and a return stroke each time said selectively actuatable staple ejecting means is actuated, the drive stroke of said ram being such that said ram will sequentially (1) cause said bridge of said staple to engage said anvil and said legs of said staple to be deformed along a curved path under said anvil so that said legs pass through said staple ejection aperture and engage and draw together tissue disposed beneath said staple ejection aperture, and (2) cause said bridge of said staple to force said anvil and said staple supporting means to a second position that is far enough away from said first position to allow the bridge of said staple to pass by said anvil and out of said staple ejection aperture.

2. A stapler system according to claim 1 wherein said anvil has a convex surface that is engaged by the bridge of a staple as said staple is driven out of said ejection aperture.

3. A stapler system according to claim 1 wherein said stapler further comprises operating means for selectively operating said staple ejecting means.

4. A stapler system according to claim 1 wherein said stapler body further comprises a front wall, and further wherein said anvil contacts said front wall when said staple supporting means is in its said first position, and said anvil is separated from said front wall by a gap at least equal to the thickness of the bridge of one of said plurality of staples when said staple supporting means is in its said second position.

5. A stapler system according to claim 4 wherein said front wall has interior and exterior surfaces and said ram comprises first and second plates, said ram being positioned relative to said front wall so that said first plate confronts and is slidable with respect to said interior surface of said front wall toward and away from said ejection aperture and so that said second plate confronts and is slidable with respect to said exterior surface of said front wall toward and away from said ejection aperture.

6. A stapler system according to claim 5 wherein a portion of said staple ejecting means extends into a hole in said ram when said ram is at rest.

7. A stapler system according to claim 1 wherein said pointed ends of said staple terminate above said concave bridge.

8. A stapler system according to claim 3 wherein said ram is releasably coupled to said operating means.

9. A stapler system according to claim 8 wherein said operating means comprises ram driver means for moving said ram away from said ejection aperture and for driving said ram toward said ejection aperture.

10. A stapler system according to claim 9 wherein said ram driver means comprises spring means coupled to said ram for urging said ram toward said ejection aperture.

11. A stapler system according to claim 10 wherein said operating means includes coupling means attached to said ram driver means and releasably engagable with said ram for engaging said ram when said ram is in a first position and for automatically disengaging itself from said ram when said ram is moved to a second position by said ram driver means, whereby said ram is free to be driven by said spring means toward said ejection aperture.

12. A stapler system according to claim 10 wherein said ram has an opening, and said operating means comprises a handle pivotally mounted on said body and a finger on said handle, said finger being disposed so as to extend into said opening when said stapler is in rest position and being detachable from said ram when said ram has been moved a selected distance away from said ejection aperture by pivotal movement of said handle, whereby said ram is free to be driven by said spring means in a direction to eject a staple from said stapler.

13. A stapler system according to claim 12 wherein said body has first and second side walls with openings and said handle has laterally projecting pivot members formed integral with opposite sides thereof, and further wherein said pivot members extend into said openings so as to pivotally secure said handle to said body.

14. A stapler system according to claim 13 wherein said pivot members make a snap fit in said openings.

15. A stapler system according to claim 12 wherein said handle has a cam portion engaged with said spring means and arranged so as to bias said spring means as said ram is moved away from said ejection aperture by said finger.

16. A stapler system according to claim 1 wherein said staple supporting means and said staple ejecting means have cooperating stop means for stopping said ram at a selected point as it moves toward said ejection aperture to implant a staple.

17. A stapler system according to claim 1 wherein said staple supporting means comprises a mandrel having a curved surface for supportively engaging said staples, said curved surface having a shape corresponding to the shape of said staples, said staple supporting means further comprising rod means disposed adjacent said curved surface for ensuring said staples remain engaged with said curved surface.

18. A stapler system according to claim 1 wherein said staple ejecting means comprises ram driver means for causing said ram to drive said staple into said tissue with a velocity that exceeds the dynamic resiliency of said tissue so as to minimize deformation or compacting of said tissue during insertion of said staple.

19. A stapler comprising:
a body having an ejection aperture;
staple supporting means for supporting a plurality of staples for delivery to a predetermined ejection position;
staple advancing means for advancing staples carried by said staple supporting means to said predetermined ejection position;
a staple ejecting ram reciprocally mounted to said body for driving a staple located in said ejection position through said ejection aperture and implanting it into tissue engaged by said stapler;
an anvil carried by said staple supporting means and located in the path of movement of said ram;
a spring biasing said ram toward said ejection aperture;
selectively actuatable means for causing said ram to drive a staple located in said ejection position through said ejection aperture into tissue engaged by said stapler, said selectively actuatable means comprising an operating lever pivotally attached to said body, a ram-shifting finger associated with said lever, means for (a) holding said finger in engagement with said ram as said lever is pivoted so as to cause said finger to move said ram away from said ejection aperture and (b) allowing said finger to be disengaged from said ram when said ram has been moved a selected distance away from said ejection aperture, and means associated with said lever for stressing said spring in a direction to increase its bias on said ram as said ram is moved away from said ejection aperture, whereby when said finger is disengaged from said ram said spring will propel said ram back toward said ejection aperture with a force sufficient to drive a staple located in said ejection position through said ejection aperture into tissue engaged by said stapler;
additional means supporting said staple supporting means for movement toward and away from the path of movement of said ram; and
biasing means for biasing said staple supporting means toward the path of movement of said ram, said biasing means being adapted to allow said anvil to be forced out of the path of movement of said ram by a staple driven by said ram.

20. A stapler according to claim 19 wherein said selectively actuatable means are adapted to retract said anvil at the bottom end of the staple driving stroke of said ram.

21. A stapler according to claim 20 wherein said anvil has a convex surface confronting said ram, and said ram is shaped so that a staple engaged by said ram is caused to bend around said anvil as it is driven out of said ejection aperture by said ram.

22. A method of implanting a staple in incised tissue comprising in sequence the steps of:
(a) providing a staple having a pair of oppositely curved leg sections connected by a concave bridge section;
(b) driving said staple with a selected force against an anvil positioned adjacent the incised tissue;
(c) deforming said bridge section around said anvil so as to force said leg sections to penetrate said incised tissue and to curve toward one another as they penetrate further into said tissue; and
(d) utilizing a portion of said selected force to move said anvil out from between said staple and said tissue.

23. A method according to claim 22 wherein the staple in its manufactured condition comprises curved leg sections having pointed ends, said pointed ends terminating above said bridge section, and further wherein said deforming step comprises deforming said bridge section around said anvil so that said bridge section still has a concave shape at the time that the leg sections penetrate said tissue, so that further deformation of said bridge section by said ram causes the pointed ends of said legs to move toward one another in the tissue.

* * * * *